(12) United States Patent
Helfer et al.

(10) Patent No.: US 7,389,137 B2
(45) Date of Patent: Jun. 17, 2008

(54) OPTICAL MRI CATHETER SYSTEM

(75) Inventors: Jeffrey L. Helfer, Webster, NY (US); Stuart G. MacDonald, Pultneyville, NY (US); Robert W. Gray, Rochester, NY (US); Christopher Thomas, Rochester, NY (US)

(73) Assignee: Biophan Technologies, Inc., Pittsford, NY (US)

( * ) Notice: Subject to any disclaimer, the term of this patent is extended or adjusted under 35 U.S.C. 154(b) by 632 days.

(21) Appl. No.: 11/119,677

(22) Filed: May 2, 2005

(65) Prior Publication Data

US 2005/0197563 A1    Sep. 8, 2005

Related U.S. Application Data

(62) Division of application No. 10/202,921, filed on Jul. 25, 2002, now Pat. No. 6,925,322.

(51) Int. Cl.
 *A61B 5/05* (2006.01)
 *A61B 6/00* (2006.01)
 *G01V 3/00* (2006.01)

(52) U.S. Cl. .................. 600/423; 324/318; 600/433

(58) Field of Classification Search ................ 600/423, 600/425, 422, 417, 407, 421, 410, 414, 433, 600/585; 324/318, 307, 308, 309
See application file for complete search history.

(56) References Cited

U.S. PATENT DOCUMENTS

| | | | |
|---|---|---|---|
| 3,057,356 A | 10/1962 | Greatbatch | |
| 3,478,746 A | 11/1969 | Greatbatch | |
| 3,508,167 A | 4/1970 | Russell, Jr. | |
| 3,669,095 A | 6/1972 | Kobayashi et al. | |
| 3,686,958 A | 8/1972 | Porter et al. | |
| 3,718,142 A | 2/1973 | Mulier | |
| 3,789,667 A | 2/1974 | Porter et al. | |
| 3,826,015 A | 7/1974 | Berkovits | |
| 4,012,641 A | 3/1977 | Brickerd, Jr. et al. | |
| 4,041,954 A | 8/1977 | Ohara | |

(Continued)

FOREIGN PATENT DOCUMENTS

WO    WO 01/74241    10/2001

OTHER PUBLICATIONS

A. Jerwzewski et al;, "Development of an MRI-Compatible Catheter for Pacing the Heart: Initial In Vitro and In Vivo Results," JMRI, ISHRM (US), vol. 6 (No. 6), p. 948-949, (Jun. 14, 1996).

(Continued)

*Primary Examiner*—Daniel L Robinson (57) ABSTRACT

An assembly for delivering optical signals comprising a nuclear magnetic resonance system comprised of magnets, an NMR programmable logic unit, a signal input channel, and a command output channel; an optical interface assembly electrically connected to the nuclear magnetic resonance system, the optical interface assembly comprising a first laser modulated so as to produce laser optical signals, an interface optical to electrical signal convertor; and a catheter assembly connected to said optical interface assembly, the catheter assembly comprising a proximal end, a distal end, a fiber optic cable assembly, an electronics assembly disposed at the distal end comprised of a catheter electrical to optical signal convertor and a catheter optical to electrical signal convertor, and a first receiving coil disposed at the distal end.

21 Claims, 9 Drawing Sheets

U.S. PATENT DOCUMENTS

| | | |
|---|---|---|
| 4,050,004 A | 9/1977 | Greatbatch |
| 4,071,032 A | 1/1978 | Schulman |
| 4,091,818 A | 5/1978 | Brownlee et al. |
| 4,200,110 A | 4/1980 | Peterson et al. |
| 4,210,029 A | 7/1980 | Porter |
| 4,254,776 A | 3/1981 | Tanie et al. |
| 4,325,382 A | 4/1982 | Miodownik |
| 4,333,053 A | 6/1982 | Harrison et al. |
| 4,341,221 A | 7/1982 | Testerman |
| 4,379,262 A | 4/1983 | Young |
| 4,432,363 A | 2/1984 | Kakegawa |
| 4,450,408 A | 5/1984 | Tiemann |
| 4,476,870 A | 10/1984 | Peterson et al. |
| 4,491,768 A | 1/1985 | Slicker |
| 4,545,381 A | 10/1985 | Bournay, Jr. et al. |
| 4,611,127 A | 9/1986 | Ibrahim et al. |
| 4,677,471 A | 6/1987 | Takamura et al. |
| 4,686,964 A | 8/1987 | Yunoki et al. |
| 4,691,164 A | 9/1987 | Haragashira |
| 4,719,159 A | 1/1988 | Clark et al. |
| 4,727,874 A | 3/1988 | Bowers et al. |
| 4,763,075 A | 8/1988 | Weigert |
| 4,784,461 A | 11/1988 | Abe et al. |
| 4,798,443 A | 1/1989 | Knipe et al. |
| 4,800,883 A | 1/1989 | Winstrom |
| 4,804,244 A | 2/1989 | Hasegawa et al. |
| 4,827,906 A | 5/1989 | Robicsek et al. |
| 4,827,934 A | 5/1989 | Ekwall |
| 4,858,610 A | 8/1989 | Callaghan et al. |
| 4,879,992 A | 11/1989 | Nishigaki et al. |
| 4,880,004 A | 11/1989 | Baker, Jr. et al. |
| 4,903,701 A | 2/1990 | Moore et al. |
| 4,911,525 A | 3/1990 | Hicks et al. |
| 4,930,521 A | 6/1990 | Metzger et al. |
| 4,934,785 A | 6/1990 | Mathis et al. |
| 4,987,897 A | 1/1991 | Funke |
| 4,991,590 A | 2/1991 | Shi |
| 5,010,888 A | 4/1991 | Jadvar et al. |
| 5,055,810 A | 10/1991 | deLaChapelle et al. |
| 5,058,586 A | 10/1991 | Heinze |
| 5,061,680 A | 10/1991 | Paulson et al. |
| 5,089,697 A | 2/1992 | Prohaska |
| 5,113,859 A | 5/1992 | Funke |
| 5,131,409 A | 7/1992 | Lobarev et al. |
| 5,154,387 A | 10/1992 | Trailer |
| 5,158,932 A | 10/1992 | Hinshaw et al. |
| 5,168,871 A | 12/1992 | Grevious |
| 5,178,149 A | 1/1993 | Imburgia et al. |
| 5,214,730 A | 5/1993 | Nagasawa et al. |
| 5,217,009 A | 6/1993 | Kronberg |
| 5,217,010 A | 6/1993 | Tsitlik et al. |
| 5,226,210 A | 7/1993 | Koskenmaki et al. |
| 5,240,004 A | 8/1993 | Walinsky et al. |
| 5,243,979 A | 9/1993 | Stein et al. |
| 5,265,602 A | 11/1993 | Anderson et al. |
| 5,267,564 A | 12/1993 | Barcel et al. |
| 5,324,310 A | 6/1994 | Greeninger et al. |
| 5,330,512 A | 7/1994 | Hauck et al. |
| 5,348,010 A | 9/1994 | Schnall et al. |
| 5,354,220 A | 10/1994 | Ganguly et al. |
| 5,370,668 A | 12/1994 | Shelton |
| 5,387,229 A | 2/1995 | Poore |
| 5,387,232 A | 2/1995 | Trailer |
| 5,402,070 A | 3/1995 | Shelton et al. |
| 5,410,413 A | 4/1995 | Sela |
| 5,415,653 A | 5/1995 | Wardle et al. |
| 5,425,373 A | 6/1995 | Causey, III |
| 5,435,308 A | 7/1995 | Gallup et al. |
| 5,435,316 A | 7/1995 | Kruse |
| 5,438,987 A | 8/1995 | Thacker et al. |
| 5,445,151 A | 8/1995 | Darrow et al. |
| 5,453,838 A | 9/1995 | Danielian et al. |
| 5,456,698 A | 10/1995 | Byland et al. |
| 5,464,014 A | 11/1995 | Sugahara |
| 5,476,095 A | 12/1995 | Schnall et al. |
| 5,520,190 A | 5/1996 | Benedict et al. |
| 5,523,534 A | 6/1996 | Meister et al. |
| 5,569,158 A | 10/1996 | Suzuki et al. |
| 5,570,671 A | 11/1996 | Hickey |
| 5,574,811 A | 11/1996 | Bricheno et al. |
| 5,575,772 A | 11/1996 | Lennox |
| 5,582,170 A | 12/1996 | Soller |
| 5,590,227 A | 12/1996 | Osaka et al. |
| 5,601,611 A | 2/1997 | Fayram et al. |
| 5,603,697 A | 2/1997 | Grundy et al. |
| 5,604,433 A | 2/1997 | Theus et al. |
| 5,611,016 A | 3/1997 | Fangmann et al. |
| 5,619,605 A | 4/1997 | Ueda et al. |
| 5,626,618 A | 5/1997 | Ward et al. |
| 5,626,619 A | 5/1997 | Jacobson et al. |
| 5,631,988 A | 5/1997 | Swirhun et al. |
| 5,634,720 A | 6/1997 | Gallup et al. |
| 5,649,965 A | 7/1997 | Pons et al. |
| 5,653,735 A | 8/1997 | Chen et al. |
| 5,654,317 A | 8/1997 | Fujioka et al. |
| 5,658,966 A | 8/1997 | Tsukamoto et al. |
| 5,679,026 A | 10/1997 | Fain et al. |
| 5,683,435 A | 11/1997 | Truex et al. |
| 5,697,958 A | 12/1997 | Paul et al. |
| 5,699,801 A | 12/1997 | Atalar et al. |
| 5,709,225 A | 1/1998 | Budgifvars et al. |
| 5,716,386 A | 2/1998 | Ward et al. |
| 5,723,856 A | 3/1998 | Yao et al. |
| 5,733,247 A | 3/1998 | Fallon |
| 5,738,105 A | 4/1998 | Kroll |
| 5,749,910 A | 5/1998 | Brumwell et al. |
| 5,752,977 A | 5/1998 | Grevious et al. |
| 5,755,739 A | 5/1998 | Sun et al. |
| 5,755,742 A | 5/1998 | Schuelke et al. |
| 5,759,197 A | 6/1998 | Sawchuk et al. |
| 5,761,354 A | 6/1998 | Kuwano et al. |
| 5,766,227 A | 6/1998 | Nappholz et al. |
| 5,772,604 A | 6/1998 | Langberg et al. |
| 5,774,501 A | 6/1998 | Halpern et al. |
| 5,776,167 A | 7/1998 | Levine et al. |
| 5,776,168 A | 7/1998 | Gunderson |
| 5,782,241 A | 7/1998 | Felblinger et al. |
| 5,782,880 A | 7/1998 | Lahtinen et al. |
| 5,808,730 A | 9/1998 | Danielian et al. |
| 5,814,087 A | 9/1998 | Renirie |
| 5,814,089 A | 9/1998 | Stokes et al. |
| 5,814,090 A | 9/1998 | Latterell et al. |
| 5,814,091 A | 9/1998 | Dahlberg et al. |
| 5,817,130 A | 10/1998 | Cox et al. |
| 5,817,133 A | 10/1998 | Houben |
| 5,817,136 A | 10/1998 | Nappholz et al. |
| 5,818,990 A | 10/1998 | Steijer et al. |
| 5,827,195 A | 10/1998 | Lander |
| 5,827,997 A | 10/1998 | Chung et al. |
| 5,830,209 A | 11/1998 | Savage et al. |
| 5,836,895 A | 11/1998 | Ramsey, III |
| 5,861,012 A | 1/1999 | Stroebel |
| 5,865,839 A | 2/1999 | Doorish |
| 5,867,361 A | 2/1999 | Wolf et al. |
| 5,868,664 A | 2/1999 | Speier et al. |
| 5,869,412 A | 2/1999 | Yenni, Jr. et al. |
| 5,870,272 A | 2/1999 | Seifried et al. |
| 5,871,509 A | 2/1999 | Noren |
| 5,871,512 A | 2/1999 | Hemming et al. |
| 5,873,898 A | 2/1999 | Hemming et al. |
| 5,882,108 A | 3/1999 | Fraizer |
| 5,882,305 A | 3/1999 | Dumoulin et al. |
| 5,891,171 A | 4/1999 | Wickham |
| 5,895,980 A | 4/1999 | Thompson |

| Patent | Date | Inventor |
|---|---|---|
| 5,897,577 A | 4/1999 | Cinbis et al. |
| 5,899,927 A | 5/1999 | Ecker et al. |
| 5,902,326 A | 5/1999 | Lessar et al. |
| 5,916,162 A | 6/1999 | Snelten et al. |
| 5,916,237 A | 6/1999 | Schu |
| 5,917,625 A | 6/1999 | Ogusu et al. |
| 5,919,135 A | 7/1999 | Lemelson |
| 5,928,145 A | 7/1999 | Ocali et al. |
| 5,928,270 A | 7/1999 | Ramsey, III |
| 5,928,570 A | 7/1999 | Reo |
| 5,940,554 A | 8/1999 | Chang et al. |
| 5,946,086 A | 8/1999 | Bruce |
| 5,951,596 A | 9/1999 | Bellinger |
| 5,954,660 A | 9/1999 | Legay et al. |
| 5,957,857 A | 9/1999 | Hartley |
| 5,963,034 A | 10/1999 | Mahapatra et al. |
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. |
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Alled, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | delValle et al. |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley |
| 6,129,745 A | 10/2000 | Sun et al. |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Ken Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |
| 6,216,041 B1 | 4/2001 | Tierney et al. |
| 6,223,083 B1 | 4/2001 | Rosar |
| 6,226,545 B1 | 5/2001 | Gilderdale |
| 6,230,060 B1 | 5/2001 | Mawhinney |
| 6,236,879 B1 | 5/2001 | Konings |
| 6,238,686 B1 | 5/2001 | Burrell et al. |
| 6,240,317 B1 | 5/2001 | Villaseca et al. |
| 6,245,020 B1 | 6/2001 | Moore et al. |
| 6,246,910 B1 | 6/2001 | Bonnet et al. |
| 6,247,474 B1 | 6/2001 | Greeninger et al. |
| 6,254,632 B1 | 7/2001 | Wu et al. |
| 6,256,537 B1 | 7/2001 | Stoop et al. |
| 6,256,541 B1 | 7/2001 | Heil et al. |
| 6,258,087 B1 | 7/2001 | Edwards et al. |
| 6,259,843 B1 | 7/2001 | Kondo |
| 6,259,954 B1 | 7/2001 | Conger et al. |
| 6,263,229 B1 | 7/2001 | Atalar et al. |
| 6,263,242 B1 | 7/2001 | Mika et al. |
| 6,266,555 B1 | 7/2001 | Werner et al. |
| 6,266,563 B1 | 7/2001 | Ken Knight et al. |
| 6,266,564 B1 | 7/2001 | Hill et al. |
| 6,266,566 B1 | 7/2001 | Nichols et al. |
| 6,270,457 B1 | 8/2001 | Bardy |
| 6,270,831 B2 | 8/2001 | Kumar et al. |
| 6,272,377 B1 | 8/2001 | Sweeney et al. |
| 6,272,380 B1 | 8/2001 | Warman et al. |
| 6,274,265 B1 | 8/2001 | Kraska et al. |
| 6,275,730 B1 | 8/2001 | Ken Knight et al. |
| 6,275,732 B1 | 8/2001 | Hsu et al. |
| 6,275,734 B1 | 8/2001 | McClure et al. |
| 6,277,078 B1 | 8/2001 | Porat et al. |
| 6,277,107 B1 | 8/2001 | Lurie et al. |
| 6,278,057 B1 | 8/2001 | Avellanet |
| 6,278,277 B1 | 8/2001 | Zeiger |
| 6,278,894 B1 | 8/2001 | Salo et al. |
| 6,278,897 B1 | 8/2001 | Rutten et al. |
| 6,296,654 B1 | 10/2001 | Ward |
| 6,317,633 B1 | 11/2001 | Jorgenson et al. |
| 6,343,227 B1 * | 1/2002 | Crowley ..................... 600/407 |
| 6,367,984 B1 | 4/2002 | Stephenson et al. |
| 6,411,838 B1 * | 6/2002 | Nordstrom et al. ......... 600/476 |
| 6,438,206 B1 * | 8/2002 | Shinar et al. ................ 378/123 |
| 6,493,573 B1 | 12/2002 | Martinelli et al. |
| 6,535,755 B2 | 3/2003 | Enholm |
| 6,537,232 B1 | 3/2003 | Kucharczyk et al. |
| 6,584,343 B1 | 6/2003 | Ransbury et al. |
| 6,636,757 B1 | 10/2003 | Jascob et al. |
| 6,658,279 B2 * | 12/2003 | Swanson et al. ............ 600/407 |
| 6,925,322 B2 | 8/2005 | Helfer |
| 6,980,848 B2 | 12/2005 | Helfer |
| 7,302,289 B2 * | 11/2007 | Crowley ..................... 600/478 |
| 2002/0116033 A1 * | 8/2002 | Greatbatch et al. ........... 607/33 |

OTHER PUBLICATIONS

W. Moshage et al., "A Non-Magnetic, MRI Compatible Pacing Center for Clinical Application In Magnetocardiography," Biomedizinixche Technik Band, Erganzungsband (Germany), p. 162-163, (Jun. 14, 1990).

C. Roos, et al., "Fiber Optic Pressure Transducer for Use Near MR Magnetic Fields," RSNA 1985; one page.

K. Wickersheim et al., "Fiberoptic Thermometry and its Applications," J. Microwave Power (1987); pp. 85-94.

Mark B. M. Hofman;"MRI-Compatible Cardiac Pacing Catheter," JMRI; May/Jun. 1997; p. 612.

A.A. Damji et al., "RF Interference Suppression in a Cardiac Synchronization System Operating in High Magnetic Field NMR Imaging System," Magnetic Resonance Imaging, vol. 6, pp. 637-640, (1988).

Frank G. Shellock et al., "Burns Associated with the use of Monitoring Equipment during MR Procedures," JMRI, Jan./Feb. 1998; pp. 271-272.

J. Nyenhuis et al., "Heating Near Implanted Medical Devices by the MRI RF-Magnetic Field," IEEE Trans. Mag.; Sep. 1999; four pages.

Frank Shellock et al., "Cardiovascular Catheters and Accessories: Ex Vivo Testing of Ferromagnetism, Heating, and Artifacts Associated with MRI," JMRI, Nov./Dec. 1998, vol. 8 #6; pp. 1338-1342.

J. Rod Gimbel et al., "Safe Performance of Magnetic Resonance," PACE; vol. 19; Jun. 1996; pp. 913-919.

National Library of Medicine: "Rapid Ventricular Pacing in a Pacemaker Patient Undergoing Magnetic Resonance Imaging," Pub Med; Pacing Clin Electrophysiol; Jun. 1998; p. 1.

National Library of Medicine;"Effects of Magnetic Resonance Imaging on Cardiac Pacemakers and Electrodes," Pub Med; Am Heart J; (1997); pp. 1-2.

M. Kusumoto et al., "Cardiac Pacing for the Clinician," Lippincott Williams & Wilkins: (2001); Chapter 1, pp. 9, 12, 13, 18, 22, 24.

Donald Fink; "Electronic Engineering," Electronic Engineers Handbook; 2nd edition, Megraw Hill; (1982); Section 14; pp. 29-45.

X Luo et al., "Eletcromagnetic Interference Shielding Using Continuous Carbon-Fiber Carbon-Matrix and Polymer-Matrix Composites," Composites Part B: Engineering: (1999); pp. 227-231.

D.D.L. Chung, "Flexible Graphile for Gasketing, Absorption, Electromagnetic Interference Shielding, Vibration Damping, Electrochemical Applications, and Stress Sensing," Journal of Materials Engineering and Performance; Apr. 2000; vol. 9 p. 161-163.

M. Konings et al., "Catheters and Guidewires In Inerventional MRI; Problems and Solutions," Medical Mundi; 45/1; Mar. (2001).

M. Konings; "Development of an MR-Safe Tracking Catheter with a Laser DrivenTip Coil," Journal of Magnetic Resonance Imaging 2001:13:131-135. c. 2001 Wiley-Liss, Inc.

Ey Yong et al., "An Optical System for Wireless Detuning of Parallel Resonant Circuits" Journal of Magnetic Resonance Imaging; (2000); vol. 12, pp. 632-638.

Bernd Nowak; "Taking Advantage of Sophisticated Pacemaker Diagnostics," Excerpts Medica; (1999); pp. 172D-179D.

Jose A. Jogler et al., "Interaction of a Commercial Heart Rate Monitor With Implanted Pacemakers," Excerpta Medica; (1999); pp. 790-792.

J.A. Pomposo et al., "Polypyrrole-based Conducting Hol Melt Adhesives for EMI Shielding Applications," Elsevier; Synthetic Metals 104; (1999); pp. 107-111.

K. Grattan et al., "Fiber Optic Sensor Technology: An Overview," Elsevier; Sensors and Actuators 82; (2000);pp. 40-61.

L. Rippert et al., "Optical and Acoustic Damage Detection in Laminated CFRP Composite Materials," Elsevier; Composites Science and Technology 60: (2000); pp. 2713-2724.

C. Strandman et al., "A Production Process of Silicon Sensor Elements for a Fibe-Optic Pressure Sensor," Elsevier; Sensors and Actuators A63; (1997); pp. 69-74.

D. Howard et al., "A Single-Fringe Etaion Silicon Pressure Transducer," Elsevier; Sensors and Actuators 86; (2000); pp. 21-25.

Dan Haronian, "Displacement Sensing Using Geometrical Modulation in Reflection Mode (GM-RM) of Coupled Optical Waveguides," J. Micromech, Microeng., (UK), (1998); pp. 323-326.

H Ghafouri-Shiraz, "A Novel Distributed Feedback Laser Diode Structure foran Optical Wavelength Tunable Filter," Semicond. Sci. Technol. 12; (UK), (1997); pp. 1161-1165.

L. Kasarian, "A New Optical Fiber Multiplexer for Distortion-Free Light Transfer in Multichannel Fiber Optic Sensor Systems," Elsevier; Sensors and Actuators 84; (2000); pp. 250-258.

X. Yan et al., "Electric Field Controlled 2×2 Bypass Exchange Photorefractive Switch," IOP Publishing; (UK) (1996), pp. 383-386.

E. Piener et al., "A Micromachined Vibration Sensor Based on the Control of Power Transmitted Between Optical Fibres," Elsevier; Sensors and Actuators A65; (1998) pp. 23-29.

D. Sun et al., "High Performance Unidirectional Electrooptic Modulator Based On Polymeric Highly Multi-Mode Waveguides,"Elsevier; Optics & Laser Technology 30; (1998); 481-489.

Engin Molva; "Microchip Lasers and Their Applications in Optical Microsystems," Elsevier; Optical Materials 11; (1999); pp. 289-299.

J. Linares et al., "Theory and Design of an Integrated Optical Sensor Based on Planer Waveguiding Lenses," Elsevier; Optics Communications 180; (2000); pp. 29-36.

O. Parriaux et al., "Coupling Gratings as Waveguide Functional Elements," IOP Publishing; Pure Appl. Opt. 5; (1996); pp. 453-469.

E T Enikov et al., "Three-Dimensional Microfabrication for a Multi-Degree of Freedom Capacitive Force Sensor Using Fibre-Chip Coupling" IOP Publishing; (UK); J. Micromechi. Microeng. 10;(2000) pp. 492-497.

J. Holm et al., "Through-Etched Silicon Carriers for Passive Alighnment of Optical Fibere to Surface-Active Optoelectronic Components" Elsevier;Sensors and Actuators 82; (2000) pp. 245-248.

M. Kimura et al., "Vibration Sensor Using Optical-Fiber Catilever with Bulb-Lens" Elsevier: Sensors and Actuators A66; (2000) pp. 178-183.

Y. Mao et al., "Three-Stage Wavelength Converter Based on Cross-Grain Modulation in Semiconductor Optical Amplifiers"Elsevier; Optics Communications 167; (1999) pp. 57-68.

X. Hu et al., "Dynamically Induced Irreversibility; Light Amplication and Quantum Noise Reduction in a V-Type Three-Level System" IOP Publishing; J. Opt B: Quantum Semiclass. Opt. 2; (UK) (2000); pp. 570-575.

Y. Yim et al., "Lithium Niobate Integrated-Optic Voltage Sensorwith Variable Sensing Ranges" Elsevier; Optical Communications 152; Jul. 1, 1998; pp. 225-228.

C. Lee et al., "Electromagnetic Interference Shilding Efficiency of Polyanllin Mixtures and Mutilayer Films" Elsevier; Synthetic Metals 102; (1999) pp. 1346-1349.

Marc Desmulliez, "Optoelectronics-VLSI System Integration Technological Challenges" Elsevier; Materials Science and Engineering B74;(2000) pp. 269-275.

J. Zook et al., "Fiber-optic Vibration Sensor Baed on Frequency Modulation of Light-Excited Oscillators" Elsevier; Sensors and Actuators 83; (2000); pp. 270-276.

M. Reta-Hernandez et al., "Attenuation of Low Frequency Magnetic Fields Using Active Shielding" Elsevier; Electric Power Systems Research 45; (1998); pp. 57-63.

C. Huang et al., "The EMI Shielding Effectiveness of PC/ABS/Nickel-Coated Carbon-Fibre Composites" Elsevier; European Polymer Journal 36; (2000) pp. 2727-2737.

M. Balucani et al., "Optical Link for DigitalTransmissions Using Porou Silicon Light Emitting Diode" Elsevier; Journal of Non-Crystalline Solids 266-269; (2000) pp. 1238-1240.

D. Egelman et al., "Calcium Dynamics in the Extracellular Space of Mammalian Nerual Tissue" Biophysical Journal; vol. 76; Apr. 1999; pp. 1856-1867.

* cited by examiner

OPTICAL MRI CATHETER SYSTEM

CROSS-REFERENCE TO RELATED PATENT APPLICATIONS

This application is a divisional application of patent application U.S. Ser. No. 10/202,921, filed on Jul. 25, 2002 now U.S. Pat. No. 6,925,322, the disclosure of which is incorporated herein by reference.

BACKGROUND OF THE INVENTION

1. Field of the Invention

An invasive apparatus for receiving a magnetic resonance signal from within a body and providing means for transmitting the signal to the received signal input channel of standard magnetic resonance systems.

2. Description of Related Art

Magnetic resonance imaging ("MRI") has been developed as an imaging technique adapted to obtain both images of anatomical features of human patients as well as some aspects of the functional activities and characteristics of biological tissue. These images and/or functional and/or chemical measurements have medical diagnostic value in determining the state of the health of the tissue examined.

In an MRI process, a patient is typically aligned to place the portion of the patient's anatomy to be examined in the imaging volume of the MRI apparatus. Such an MRI apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). A magnetic field gradient ($\Delta B_0/\Delta x_i$) refers to the variation of the field along the direction parallel to $B_0$ with respect to each of the three principal Cartesian axes, $x_i$. The apparatus also comprises one or more RF (radio frequency) coils which provide excitation and detection of the MRI signal. Additionally or alternatively, detection coils may be designed into the distal end of a catheter to be inserted into a patient. When such catheters are employed, their proximal ends are connected to the signal input channel of the magnetic resonance imaging device. The detected signal is transmitted along the length of the catheter from the receiving antenna and/or receiving coil in the distal end to the MRI input channel connected at the proximal end.

The insertion of metallic wires into a body, e.g. catheters and guidewires, while in a magnetic resonance imaging environment, poses potentially deadly hazards to the patient through excessive heating of the wires, e.g. in excess of 74° C. in some studies. M. K. Konings, et. al, in "Catheters and Guidewires in Interventional MRI: Problems and Solutions", MEDICA MUNDI 45/1 March 2001, list three ways in which conductors may heat up in such environments: 1) eddy currents, 2) induction loops, and 3) resonating RF transverse electromagnetic (TEM) waves along the length of the conductors. They write "Because of the risks associated with metal guidewires, and catheters with metal conductors, in the MRI environment, there is an urgent need for a non-metallic substitute, both for guidewires and for signal transfer." They further propose the use of ". . . a full-glass guidewire with a protective polymer coating . . . ."

The tracking and placement of a catheter within a body is an important aspect of using catheters in magnetic resonance imaging procedures. Considering the dangers inherent in the use of metallic wires in the magnetic resonance imaging environment, as mentioned above, M. K. Konings, et. al., in their paper "Development of an MR-Safe Tracking Catheter With a Laser-Driven Tip Coil" describe the design of a tracking catheter ". . . using an optical fiber with a light-diffusing tip segment to transport laser energy through the catheter. This energy is converted to a DC current running through a small coil at the catheter tip. Our method is inherently MR-safe since the use of long conducting wires is avoided."

From the paper "An Optical System for Wireless Detuning of Parallel Resonant Circuits" by E. Y. Wong, et. al., in the Journal of Magnetic Resonance Imaging 12:632-638 (2000), it is pointed out that typically when a catheter coil is used in magnetic resonance imaging, it is necessary to detune the coil away from the frequency of the magnetic resonance imaging system during the transmission of the magnetic resonance imaging pulse sequence. The authors write "In all MRI experiments in which local coils are used for signal reception, coil detuning is necessary during transmission to prevent high voltages from being induced in the receiver coil and other electronic components including the receiver preamplifier. The potentially high voltages and currents, as well as the induced electric fields, pose a safety hazard for the patient, . . . , and disrupt the desired uniform excitation field generation required for excitation; this may lead to particular localized effects in interventional or intravascular MR imaging in which small coils are used." This paper further describes the use of a complex design consisting of fiber optic cable and photoresistors to overcome these problems.

By providing a catheter with an MR receiving coil or antenna in the distal end, the coil or antenna can be placed closer to the tissue which is to be imaged or analyzed. Thus the detected signal is less susceptible to radio frequency noise. Additionally, the level of detail that can be resolved (the resolution of the image, spectrum, or other data obtained) is increased by the use of catheter coils.

Thus, it is desirable to provide an apparatus such as a catheter which can be used with a magnetic resonance system for insertion and positioning of an magnetic resonance receiver coil or antenna within a body which is not susceptible to the heating, noise pickup, electrostatic buildup and/or other hazards associated with the use of conductors in a magnetic resonance environment.

SUMMARY OF THE INVENTION

In accordance with the present invention, there is provided an assembly for delivering optical signals comprising a nuclear magnetic resonance system comprised of a magnet, an NMR programmable logic unit, a signal input channel, and a command output channel; an optical interface assembly electrically connected to the nuclear magnetic resonance system, the optical interface assembly comprising a first laser modulated so as to produce laser optical signals, an interface optical to electrical signal convertor; and a catheter assembly connected to the optical interface assembly, the catheter assembly comprising a proximal end, a distal end, a fiber optic cable assembly, an electronics assembly disposed at the distal end comprised of a catheter electrical to optical signal convertor and a catheter optical to electrical signal convertor, and a first receiving coil disposed at the distal end. The NMR programmable logic unit of the nuclear magnetic resonance system sends command signals through the command output channel to the optical interface assembly for use in modulating the first laser. The laser optical signals received through the fiber optic cable assembly from the first laser are converted into catheter electrical signals by the catheter optical to electrical signal convertor. The first receiving coil is adapted to receive electromagnetic signals and deliver coil electrical signals to the electronics assembly of the catheter assembly, and the coil electrical signals are converted by the catheter electrical to optical signal convertor to catheter optical signals and the catheter optical signals are delivered through the fiber optic cable assembly to the interface optical to electrical signal convertor. The catheter optical signals are converted by the interface optical to electrical signal convertor into interface electrical signals and are delivered to the signal input channel of the nuclear magnetic resonance system.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

Figure 1:
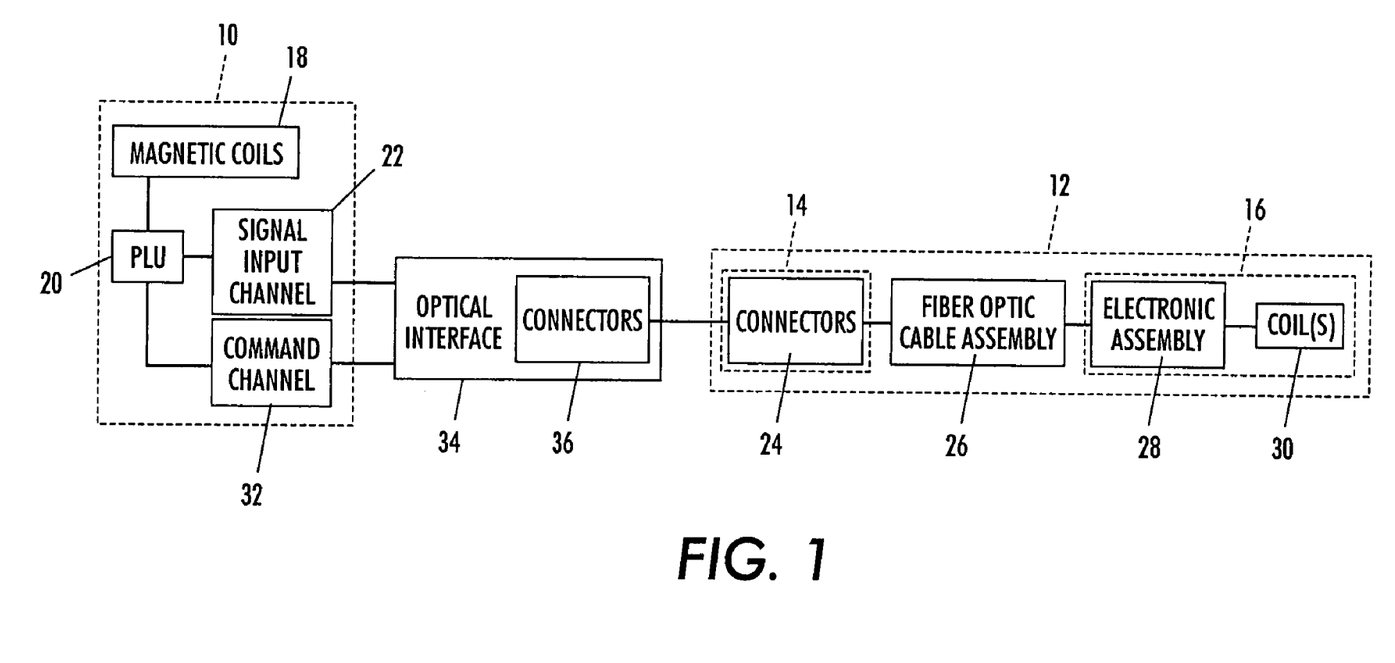
FIG. 1 is a block diagram of one preferred apparatus of the invention.

In one embodiment, the apparatus of this patent application comprises the structure shown in FIG. 1. Referring to FIG. 1, a standard magnetic resonance system 10 (e.g. the GE Signa Infinity 1.5 Tesla system, or Siemens Symphony 1.5 Tesla system) comprises means for generating and controlling magnetic fields 18, which may comprise electromagnets and/or permanent magnets, a programmable logic unit 20, a receiver input channel 22 and a command/gating output channel 32. The receiver input channel 22 is used to pass the detected signals to the programmable logic unit for image reconstruction. The command/gating output channel 32 is used to provide at minimum gating signals synchronized to the application of the gradient magnetic fields of the magnetic resonance system 10.

Continuing to refer to FIG. 1, and to the embodiment depicted therein, an optical interface assembly 34 is connected to the receiver input channel 22 and to the command/gating output channel 32 of the magnetic resonance system 10. The optical interface assembly 34 converts the electrical command/gating signals of the magnetic resonance system 10 issued through the command/gating output channel 32 into optical signals and transmits these optical signals through the catheter assembly 12. The optical interface assembly 34 also converts the optical signals received from the catheter 12 into electrical signals suitable for the magnetic resonance system's 10 receiver input channel 22.

Continuing to refer to FIG. 1, the optical interface assembly 34 is connected to the catheter assembly 12 through optical connector assembly 36 within the optical interface assembly 34 and optical connector assembly 24 in the proximal end 14 of the catheter assembly 12. Optical connectors are well known to those skilled in the arts. Reference may be had, e.g., to U.S. Pat. No. 6,149,313 (Gender selectable fiber optic connector and associated fabrication method ), which discloses "A gender selectable fiber optic connector is provided which can be readily converted between male and female configurations following assembly and polishing of the connector." U.S. Pat. No. 5,619,605 (Optical connector) discloses "A novel optical connector that includes the following: an optical connector ferrule which is capable of fixing optical fibers; optical fibers fixed onto the optical connector ferrule, such that the end surfaces of the optical fibers project beyond an end surface of the optical connector ferrule; an adhesive for fixing the optical fibers onto the optical connector ferrule; and a member whose Young's Modulus is less than that of the optical fiber and is provided to an area on the end surface of the optical connector ferrule surrounding, at a minimum, the projected portions of the optical fibers." Further reference may be had to U.S. Pat. No. 4,934,785 (Optical fiber connector), U.S. Pat. 5,963,690 (Optical fiber connector), U.S. Pat. No. 6,367,984 (Optical fiber adapter), U.S. Pat. No. 6,179,482 (Optical connector and housing for optical connector), U.S. Pat. 5,590,227 (Optical connector apparatus), U.S. Pat. No. 5,214,730 (Multifiber optical connector plug with low reflection and low insertion loss). The entire disclosure of each of these United States patents is hereby incorporated by reference into this specification.

Referring again to FIG. 1, the optical connector assemblies 36, 24 may be so constructed as to allow the catheter assembly 12 to be detached from the optical interface assembly 34. Reference may be made to U.S. Pat. No. 5,631,988 (Parallel optical interconnect) which discloses "An optical interconnect is disclosed that couples multiple optical fibers to an array of optoelectronic devices. The interconnect includes a multiple optical fiber connector and an optoelectronic board. The multiple fiber connector can be mechanically attached to or detached from the board." U.S. Pat. No. 4,804,244 (Connector for optical fiber) discloses "An optical fiber connector in which an optical fiber and an optical conversion element are detachably coupled together, and optical fibers are mutually coupled together." The entire disclosure of each of these United States patents is hereby incorporated by reference into this specification.

Continuing to refer to FIG. 1, the optical connectors 24 are fabricated to one end of the fiber optic cable assembly 26. The fiber optical cable assembly 26 may comprise one or more fiber optical strands suitable for transmitting optical signals from the distal end 16 of the catheter assembly 12 to the proximal end 14 of the catheter assembly 12. Such fiber optic cable assembly 26 is typical of prior art optical cable assemblies. Reference may be had, e.g., to U.S. Pat. Nos. 4,784,461 (optical cable with improved strength), 6,259,843 (optical cable), 5,611,016 (dispersion balanced optical cable), 4,911,525 (optical communications cable), 4,798,443 (optical cable), 5,634,720 (multi-purpose multi-parameter cardiac catheter), and the like. The entire disclosure of each of these United States patents is hereby incorporated by reference into this specification.

Additionally, fiber optic cable assembly 26 may comprise one or more lumens (not shown) suitable for the transport of a gas, e.g., air, or a liquid, e.g., a soluble drug in a saline or other solution, through the length of the catheter assembly 12. Additionally, said lumens (not shown), may allow a flexible solid material, e.g. a flexible plastic rod, to be maneuvered through the length of the catheter assembly 12. Such lumens (not shown) are well known to those skilled in the arts of catheter assemblies and are typically used to extend or retract position stabilizing balloons (not shown) or other position stabilizing means built into the catheter assembly 12. Additionally, said lumens (not shown) are used for performing biopsies, delivering stents, delivering drugs, and/or for other therapeutic purpose and/or medical procedures. Such lumens may be made from nonconductive, nonmagnetic material, e.g. plastics, or silicon dioxide, etc. Reference to such catheter assemblies may be made to International patent publication PCT WO 01/74241 A2 (Systems And Methods For Evaluating The Urethra And The Periurethral Tissues), U.S. Pat. No. 6,056,721 (Balloon catheter and method), U.S. Pat. No. 5,575,772 (Ablation catheters), U.S. Pat. No. 6,146,415 (Stent delivery system), and the like. The entire disclosure of each of these United States patents is hereby incorporated by reference into this specification.

Continuing to refer to FIG. 1 and the embodiment depicted therein, the fiber optic cable assembly 26 is connected to an electronic assembly 28 within the distal end 16 of the catheter assembly 12. The electronic assembly 28 provides the means for converting the electrical signal received by the pickup coil(s) 30 into an optical signal and to transmit said optical signal through the fiber optic cable assembly 26 to the proximal end 14 of the catheter assembly 12. Additionally, electronic assembly 28 may receive optically encoded command/gating signals which originate as electrical signals from the magnetic resonance system's 10 command/gating output channel 32, which are converted to optical command/gating signals in the optical interface 34. Said command/gating signals may be used by the electronic assembly 28 to, e.g. select which of several receiver coils 30 is to be utilized, tune and/or detune receiver coils 30 into or away from a frequency range, activate a gating switch connected to receiver coils 30, etc. Additionally or alternatively, said optical command/gating signals may be converted in total or in part into electrical power in the electronic assembly 28.

Continuing to refer to FIG. 1, the receiving catheter coils 30 may be any one of or a multiplicity of several coils and/or antenna used to receive signals from the tissues that have been excited by the magnetic resonance system 10. Various catheter coil designs are well known to those skilled in the arts. Reference may be had to, e.g., U.S. Pat. No. 6,263,229 (Miniature Magnetic Resonance Catheter Coils and Related Methods) which discloses "The present invention provides several embodiments of methods of making magnetic resonance catheter coils which include employing a flexible electrically insulative base member, depositing an electrically conductive material on the base member in a predetermined pattern to create at least one pair of generally parallel electrically conductive coil elements which are electrically connected to each other." U.S. Pat. No. 5,928,145 (Method of magnetic resonance imaging and spectroscopic analysis and associated apparatus employing a loopless antenna) discloses "The invention provides a method for magnetic resonance imaging and spectroscopic analysis of a specimen which includes positioning the specimen within a main magnetic field and introducing an antenna having a loopless antenna portion in close proximity to the specimen." U.S. Pat. No. 5,699,801 (Method of internal magnetic resonance imaging and spectroscopic analysis and associated apparatus) discloses "The invention provides a method for magnetic resonance imaging and spectroscopic analysis of the interior of a specimen which includes positioning the specimen within a main magnetic field, introducing an invasive probe having an elongated receiver coil into or adjacent to the specimen with the coil having at least one pair of elongated electrical conductors, preferably, generally parallel to each other disposed within a dielectric material and having a pair of ends electrically connected to each other. RF pulses are provided to the region of interest to excite magnetic resonance signals, gradient magnetic pulses are applied to the region of interest with the receiver coil receiving magnetic resonance signals and emitting responsive output signals which may be processed by a computer to provide image information for display in a desired manner." The entire disclosure of each of these United States patents is hereby incorporated by reference into this specification.

Figure 2:
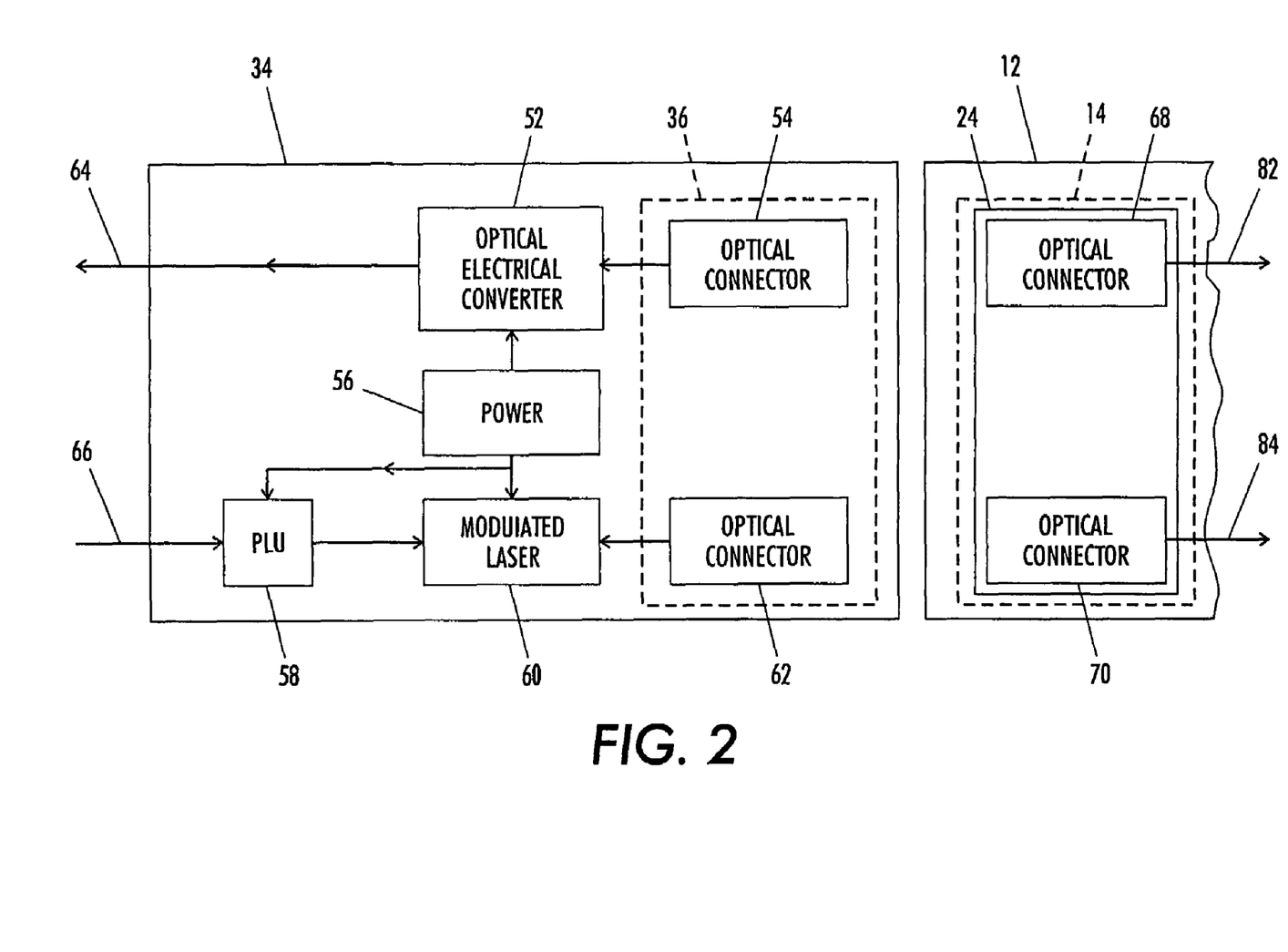
FIG. 2 is a block diagram of the Optical Interface component of the device of FIG. 1.

FIG. 2 is a schematic of an optical interface assembly 34 that may be used in the device of FIG. 1. Referring to FIG. 2, it will be seen that optical connectors 54 and 62 of the optical interface assembly 34 are the mating connectors to connectors 68 and 70. Connectors 68 and 70 comprise the proximal end 14 connector assembly 24 of the catheter assembly 12. The proximal ends of the fiber optic strands 82, 84 are connected to the optical connectors 68 and 70. Optical connectors 54, 62, 68, 70 may be, e.g., Tyco Electronic's AMP Ceramic style ST Connector part number 502579-2 or Tyco Electronic's AMP Ceramic style FC Connector Part number 504649-2. In this embodiment, optical connectors 54 and 62 comprise the connector assembly 36 of FIG. 1. Optical connector 54 is used to receive optical signals from the catheter assembly 12. Optical connector 62 is used to send optical signals through the catheter assembly 12.

Continuing to refer to FIG. 2 and to the embodiment depicted therein, the connection lines 64 and 66 are used to connect the optical interface assembly 34 to the magnetic resonance system's (10 of FIG. 1) signal input channel 22 of FIG. 1 and to the command/gating output channel 32 of FIG. 1 respectively. The connection line 64 is connected to the optical to electrical signal converter 52 component of the optical interface assembly 34. Optical to electrical signal converter 52 may be, e.g., a standard photodiode operating in a photoconductive mode. One such photodiode is UDT Sensors Inc.'s High Speed Silicon Fiber Optic Detector, part number PIN-HR020. In another preferred embodiment (not shown), optical to electrical signal converter 52 comprises electrical amplification means (not shown), e.g. and operational amplifier, and other electronic components (not shown) suitable for reproducing the original electrical signal and for matching the impedance and/or other electrical characteristics of the signal input channel 22 of FIG. 1 of the magnetic resonance system 10 of FIG. 1.

Continuing to refer to FIG. 2, the connection line 66 is connected to a programmable logic unit 58, which may be, e.g. a programmable computer, which is used to receive electrical command/gating signals from the magnetic resonance system 10 of FIG. 1 and to control the conversion of such electrical command/gating signals into optical command signals. In one embodiment, as depicted in FIG. 2, the programmable logic unit 58 is used to modulate a laser 60, such modulation in the laser's 60 light representing the converted command signal. The laser 60 may be, e.g., Sanyo's Laser Diode 785 nanometer, 25 milliWatt, part number DL4140-001. Additionally, the laser 60 is used to supply power through the catheter assembly 12 to the electronic assembly 28 of FIG. 1.

Referring to FIG. 2, the optical to electrical signal converter 52 component of the optical interface assembly 34 is used to convert the received optical signal into an electrical signal. The received optical signal may be a digital encoding of the original analog electrical signal from the coils 30 of FIG. 1, or may be analog signals representing said original electrical signal. Such analog signals may be, e.g. modulated signals in the range of about 10 mega Hertz to about 1,000 mega Hertz. The converted optical to electrical signal is then sent on to the magnetic resonance system's (10 of FIG. 1) signal input channel 22 of FIG. 1 via electrical connection 64. The optical signal received by the optical to electrical signal converter 52 originates as a picked up electrical signal induced in the coils 30 of FIG. 1 located in the distal end 16 of FIG. 1 of the catheter assembly 12. Said electrical signal is converted to an optical signal by the electronic assembly 28 of FIG. 1 located in the distal end 16 of FIG. 1 of the catheter assembly 12.

Additionally, the optical signal sent to the optical to electrical converter 52 may comprise a reference optical signal component in addition to the optically encoded received signal. Such reference signal component may be, e.g., a constant optical signal, or a saw-tooth signal. The reference component of the optical signal is used for calibration of the optical signals. The bending of the catheter assembly 12 as well as the electrical components used to generate the optical signals may introduce nonlinear effects into the produced optical signal. Such nonlinearities may be quantified by the introduction of said reference optical signal component. In the case where said reference optical signal is utilized, optical to electrical converter 52 contains means (not shown) for utilizing said reference optical signal to correct any nonlinearities induced into the received optical signal.

Continuing to refer to FIG. 2 and to the embodiment depicted therein, a power supply 56 is connected to all components of the optical interface assembly 34 which require power to operate. Power supply 56 may be, e.g., an AC to DC power converter connected to an external United States' standard 120 Volt 60 Hertz wall socket. Alternatively, power supply 56 may be a system of one or more batteries.

Figure 3:
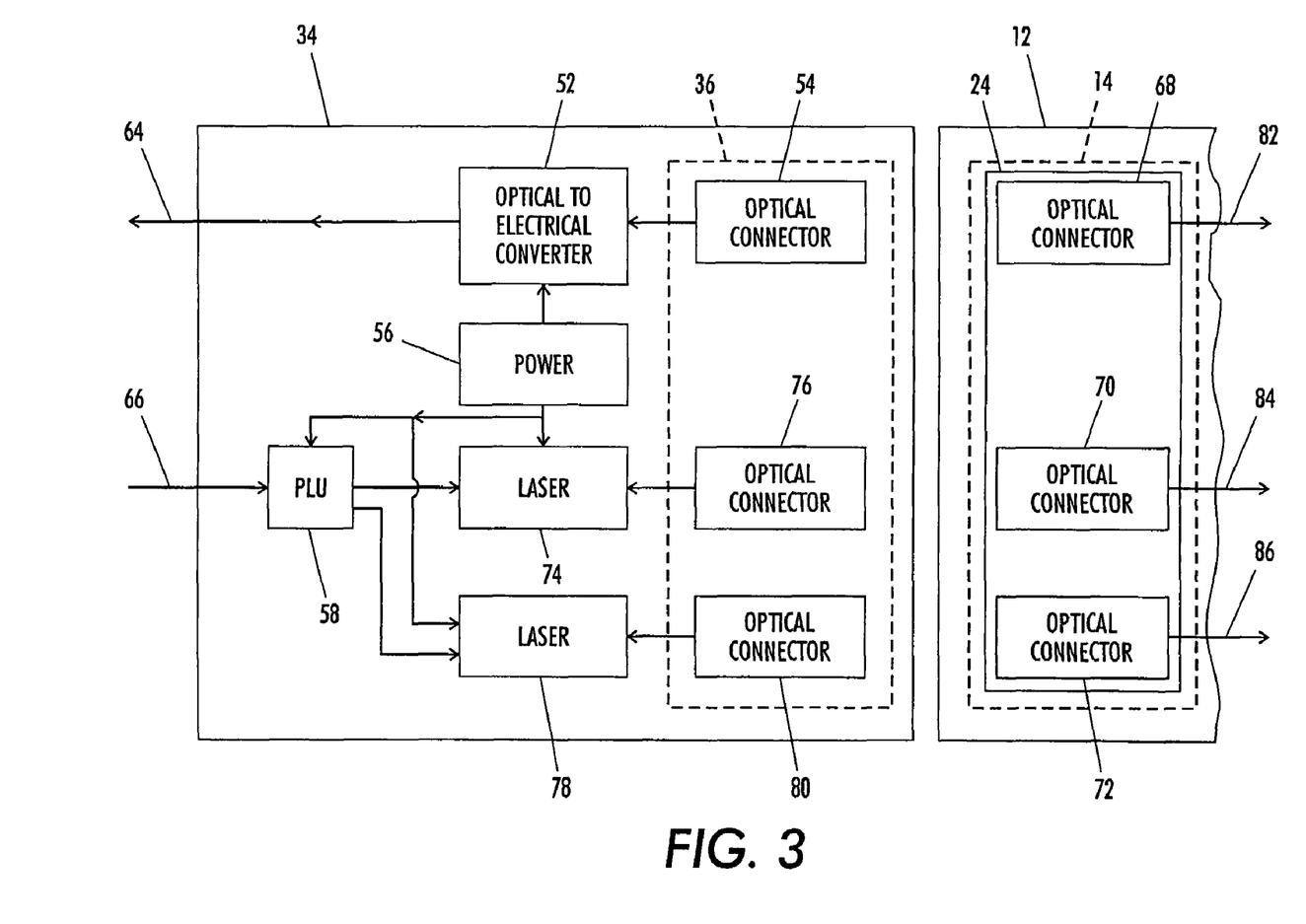
FIG. 3 is a block diagram of another Optical Interface component.

In another preferred embodiment, depicted in FIG. 3, three optical connectors 54, 76 and 80 are used to connect to the proximal end 14 of catheter assembly 12. Optical connectors 54, 76, and 80 are mated to optical connectors 68, 70, 72, respectively, in the connector assembly 24 of the proximal end 14 of the catheter assembly 12. In this embodiment, the fiber optic cable assembly 26 of FIG. 1 preferably is comprised of at least three optical fiber strands. Each strand 82, 84, 86 of the fiber optic cable assembly 26 of FIG. 1 services a different communication need.

Continuing to refer to FIG. 3, optical connectors 54 and 68 are used to connect the optical interface assembly 34 to the received signal strand 82 of the fiber optic cable assembly 26 of FIG. 1. Optical connectors 76 and 70 are used to connect the optical interface assembly 34 to the command signal strand 84 of the fiber optic cable assembly 26 of FIG. 1. Optical connectors 80 and 72 are used to connect the optical interface assembly 34 to the optical power transmission strand 86 of the fiber optic cable assembly 26 of FIG. 1. The optical power transmission strand 86 is used to deliver power to the distal end 16 of FIG. 1 of the catheter assembly 12 and in particular to the electronic assembly 28 of FIG. 1.

Continuing to refer to FIG. 3, the laser 74 is used to generate optical command/gating signals. These optical command/gating signals are used by the electronic assembly 28 of FIG. 1 to tune and/or detune and/or gate (connect/disconnect) and/or select the receiving coils 30. Laser 78 is used to generate optical power for use by the electronic assembly 28 of FIG. 1 in the distal end 16 of FIG. 1 of the catheter assembly 12. Both lasers 74 and 78 are controlled by the programmable logical unit 58 which may be, e.g. a programmable computer.

Figure 4A:
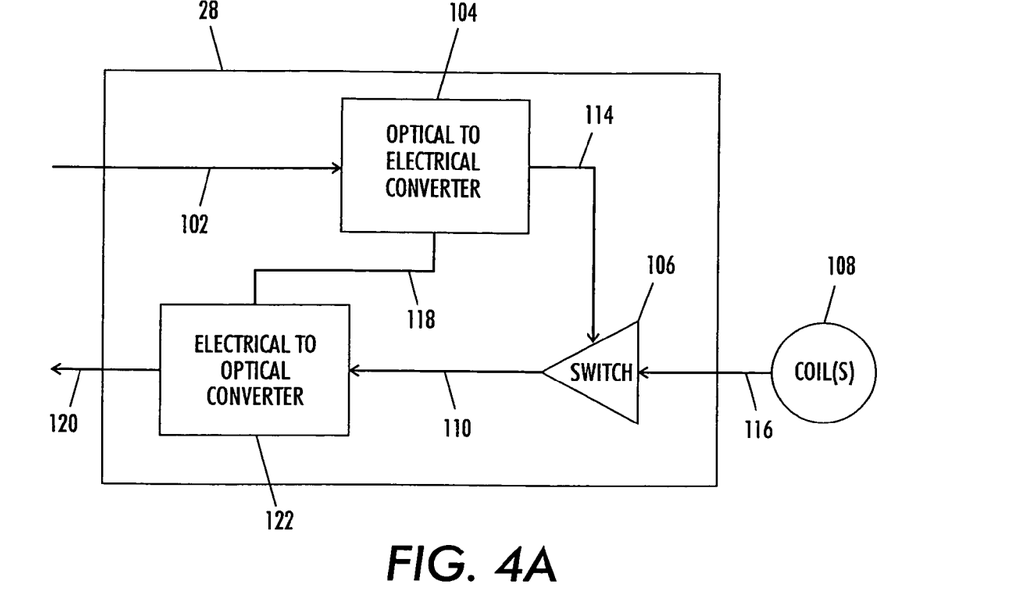
FIGS. 4 through 7 are component diagrams of the distal end of the catheter used in the device of FIG. 1.

Referring to FIG. 4A, and to the embodiment depicted therein, the components of the electronic assembly 28 of FIG. 1 are shown. An optical fiber strand 102 is connected to an optical to electrical converter 104, which is connected to a switch 106 via line 114. The optical to electrical converter 104 may be, e.g., a silicon photovoltaic cell. One such silicon photovoltaic cell can be UDT Sensors Inc.'s Planar Diffused Silicon Photodiode part number S-4CL. In one preferred method of operation, when a laser light is present at the optical to electrical converter 104, an electrical potential is applied to the switch 106, the switch 106 is open. In the absence of the laser light, and thus in the absence of an electrical potential, the switch 106 is closed.

Electronic assembly 28 also contains an electrical to optical converter 122 which converts the electrical signals received through the pickup coil(s) 108 into optical signals. Only when the switch is open may electrical signals from the coil(s) 108 reach the electrical to optical converter 122. The electrical to optical converter 122 is connected to the switch 106 via line 110 and to a fiber optic strand 120 of the fiber optic cable assembly 26 of FIG. 1. In one preferred embodiment, the electrical signals from receiving coils 108 are converted into digital optical signals. In another prefer embodiment, the electrical signals are converted into analog optical signals.

The coil(s) 108 are connected to the switch 106 via line 116. The coil(s) 108 may comprise electronic components, e.g. one or more capacitors, suitable to tune the receiving coil(s) 108 to a preferred electromagnetic frequency as well as to connect the coil(s) 108 to the electrical ground to prevent electrostatic charge from building up, as is known to those skilled in the art.

Figure 4B:
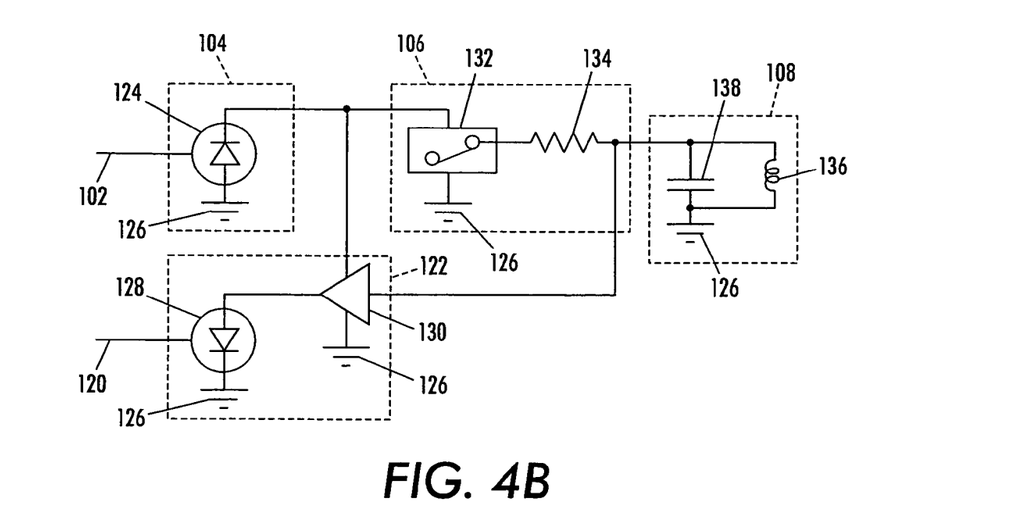

FIG. 4B illustrates one preferred electronic embodiment of the components shown in FIG. 4A. In this embodiment, the optical to electrical converter 104 consists of a silicon photovoltaic cell 124 and the catheter's common ground 126. The switch 106 comprises a normally closed switch 132, the catheter's common ground 126, and resistor 134. The electrical to optical converter 122 comprises a photo diode 128, the catheter's common ground 126, and a preamplifier 130. The coils 108 comprises a single inductive loop coil 136, a tuning capacitor 138, and the catheter's common ground 126. All such electronic components are well known to those skilled in the art.

Figure 4C:
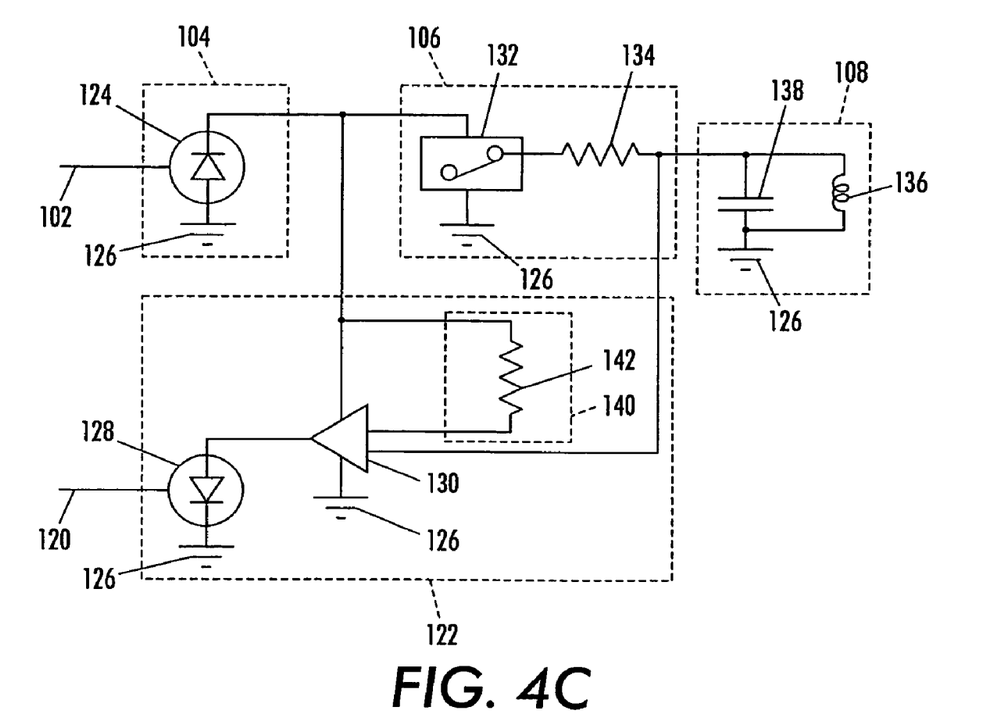

FIG. 4C illustrates another preferred electronic embodiment of the components shown in FIG. 4A. In this embodiment, the electrical to optical converter 122 further comprises a reference signal source 140 used to calibrate the received signal. In the embodiment depicted in FIG. 4C, the reference signal source comprises a resistor connected to the optical to electrical converter 104 and to the a preamplifier 130. In this arrangement, a constant signal is used for the reference calibration signal. The constant reference signal is added to the received signal. In another embodiment (not shown), a saw-tooth signal generator is used for the reference signal source 140.

In another embodiment, and continuing to refer to FIG. 4A, switch 106 is preferably a multi-state switch, used to select which of several coils 108 is to have their signals passed to the electrical to optical converter 122. The signal that the switch 106 receives from the optical to electrical converter 104 provides information indicating which of the coils 108 to connect to the electrical to optical converter 122. This is accomplished, e.g. by assigning different voltage levels to different receiver coils. For example, if the coils 108 consist of two different receiver coils (not shown), then the switch 106 is preferably a three state switch. Then an absence of any voltage from the optical to electrical converter 104 indicates the switch 106 is closed and that no receiver coil is connected to the electrical to optical converter 122. If a voltage between the range ~ to Yz Volts is applied to the switch 106, then the switch 106 connects receiver coil #1 (not shown) to the electrical to optical converter 122. Finally, if a voltage between ¾ and 1 Volts is applied to switch 106 then the switch 106 connects receiver coil #2 (not shown) to the electrical to optical converter 122.

Figure 5:
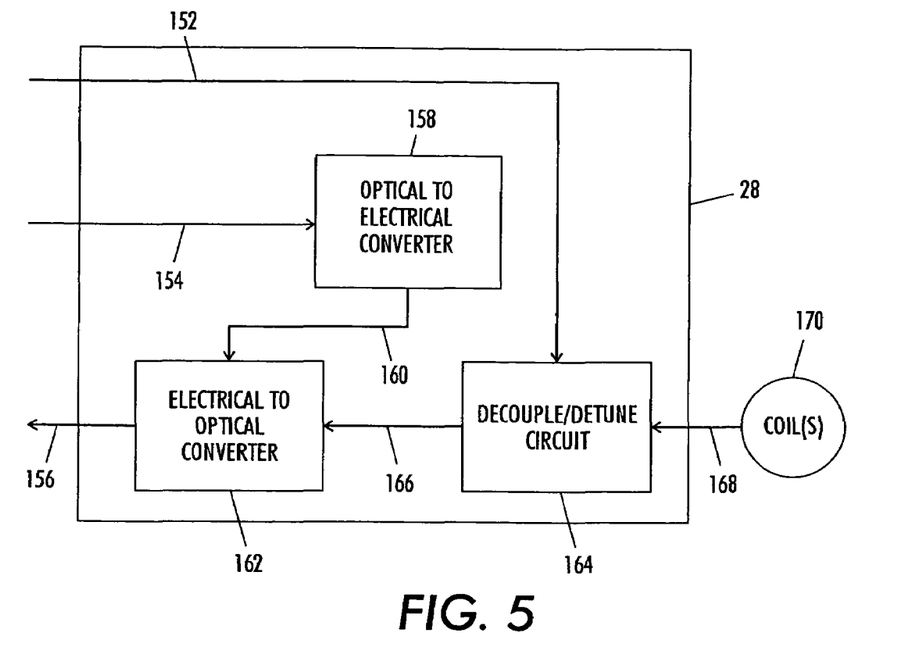

In another preferred embodiment, as depicted in FIG. 5, the electronic assembly 28 is connected to three fiber optic strands 152, 154, 156 of the fiber optic cable assembly 26 of FIG. 1. Additionally, the electronic assembly 28 is connected to the receiver coil(s) 170 via line 168.

Continuing with the preferred embodiment depicted in FIG. 5, the fiber optic strand 152 carries optical signals to the detuning assembly 164. The detuning assembly 164 may comprise, e.g. photo resistors and/or other optically active components so arranged and so connected to the receiver coil(s) 170 as to change the resonance frequency of the receiver coil(s) 170 depending on the presence or absence of light in said fiber optic strand 152. See, for example, the article "An Optical System for Wireless Detuning of Parallel Resonant Circuits" by E. Y. Wong, et. al., Journal Of Magnetic Resonance Imaging, 12:632-638 (2000) for one such detuning assembly. In another embodiment, detuning assembly 164 may comprise a switch activated by the presence or absence of a light in the optic strand 152.

Continuing with FIG. 5, the fiber optic strand 154 is used to deliver optical power to the optical to electrical converter 158. Optical to electrical converter 158 may comprise, e.g., a photovoltaic cell which converts the delivered laser light into an electrical potential difference suitable for powering other electronic components within the electronic assembly 28.

The optical to electrical converter 158 is connected to the electrical to optical converter 162 via line 160. The electrical to optical converter 162 is used to amplify and convert the electrical signal received in the coil(s) 170 into an optical signal and to transmit said optical signal through fiber optic strand 156. In one embodiment the optical signal sent through fiber optic strand 156 is a digital optical signal. In another embodiment the optical signal sent through fiber optic strand 156 is an analog optical signal.

In another embodiment, not shown, the optical to electrical converter 158 is further connected to the detuning component 164 to deliver electrical power to this component of the electronic assembly 28.

Figure 6:
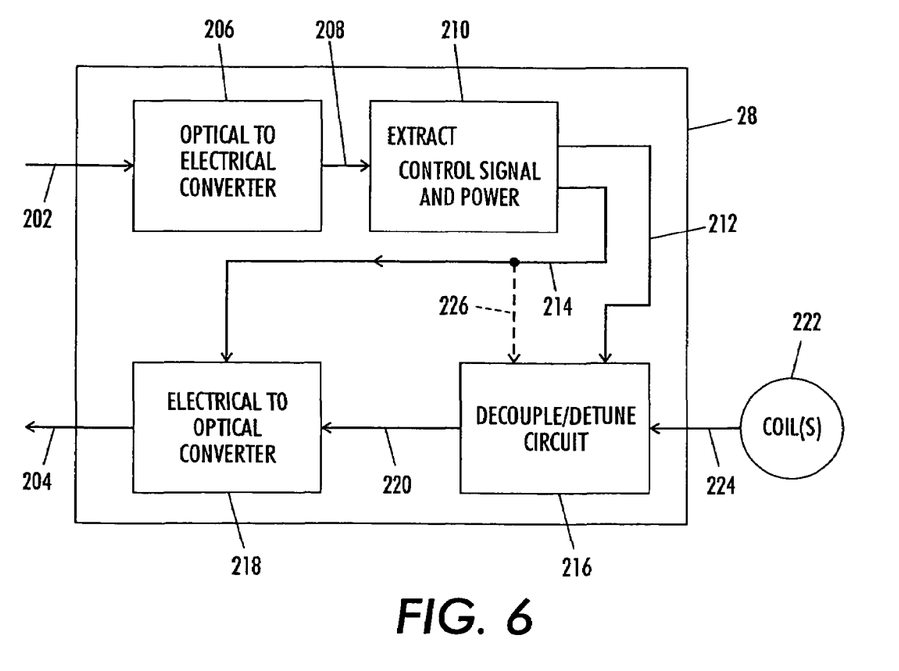

Referring to FIG. 6 and to the preferred embodiment depicted therein, the components of the electronic assembly 28 of FIG. 1 is shown. In this embodiment there are two fiber optic strands 202, 204 connecting to electronic assembly 28. Additionally, the receiver coil(s) 222 is connected to the electronic assembly 28 via line 224.

The fiber optic strand 202 carries a modulated laser light. This laser light is used to produce electrical power for the other electrical components in the electronic assembly 28 as well as to provided control signals suitable for controlling the decoupling circuit 216. The laser light traveling through fiber strand 202 is converted to an electrical signal by the optical to electrical converter 206. The optical to electrical converter 206 may comprise, e.g., a photovoltaic cell. The converted signal is passed on to the command extraction component 210 via line 208 where it is filtered for a detuning command as well as to provide power to other components within the electronic assembly 28. Any detuning command signals are sent to the decoupling component 216 via line 212. The power connection for the electrical to optical converter is provided by line 214. In one embodiment the decoupling component 216 may require electrical power. This be provided to it via optional line 226.

In one embodiment, the decoupling component 216 consists of a switch which is opened when a potential difference is provided to it via line 212 and is closed in the absence of a potential difference. In one embodiment, the decoupling component 216 comprises at least one capacitor whose capacitance changes with the application of a potential difference. In this way, the signals from line 212 change the capacitance of the receiving coil(s) 222. Thus the coils are tuned and de-tuned to receive and/or not to receive signals in a predetermined frequency range. Additionally, by actively adjusting the capacitance, the catheter assembly 12 of FIG. 1 can be utilized with any of a number of different magnetic resonance systems 10 of FIG. 1, including systems utilizing 0.5 Tesla through 7.5 Tesla magnetic fields.

Continuing to refer to FIG. 6, when the receiving coils 222 are tuned to receive a signal, or in the case of switching when the switch is opened, the received signals are passed to the electrical to optical converter 218 via conducting line 220. The electrical to optical converter 218 is delivered power via line 214. The received signal is converted to an optical signal by the electrical to optical converter 218 which is in turn sends the optical signal through fiber optic strand 204. The electrical to optical converter 218 can comprise a preamp, a reference signal generator, and other electrical components.

Figure 7:
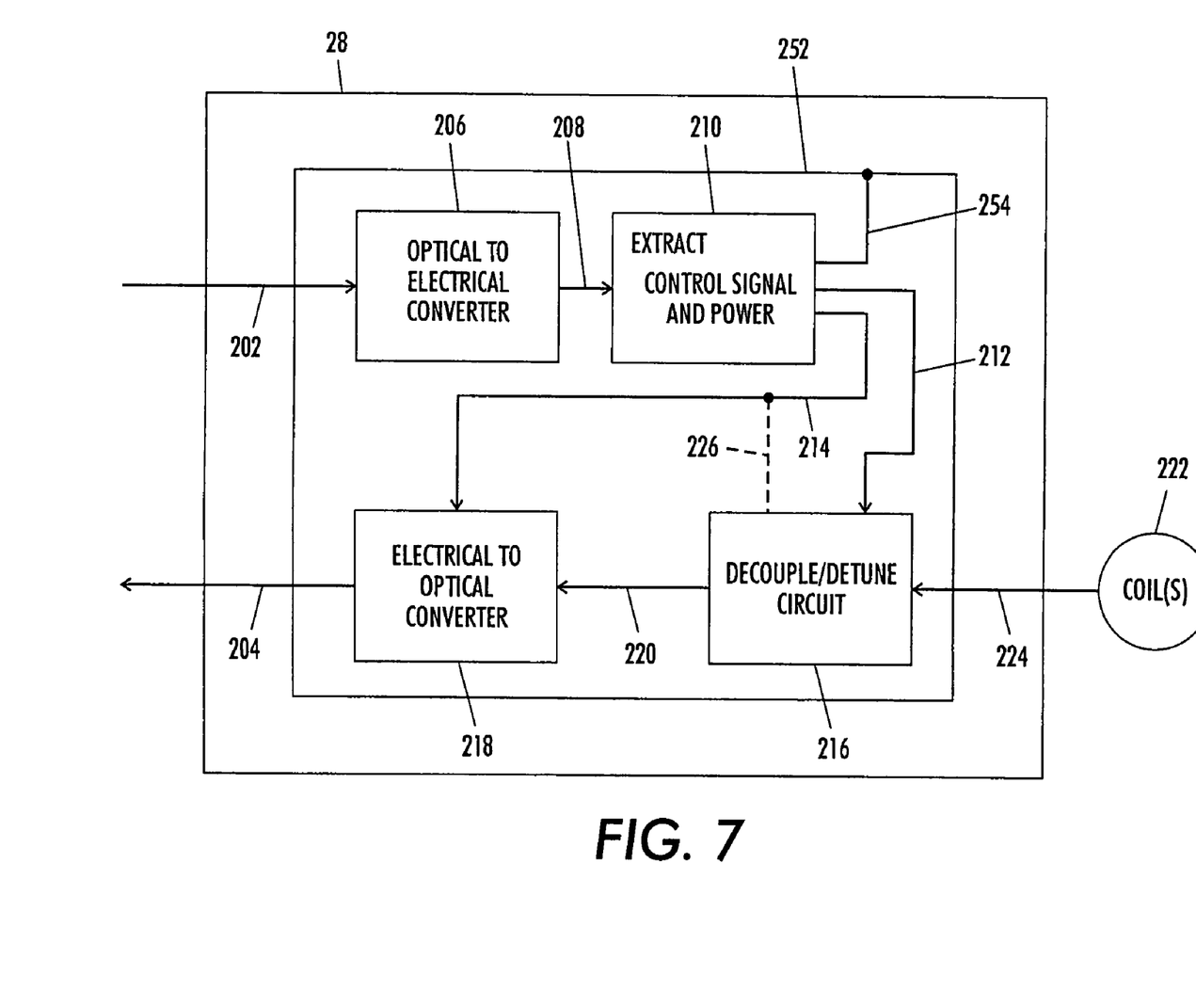

Referring to FIG. 7 and to the embodiment depicted therein, the electronic assembly 28 comprises electrical components, as in FIG. 6, contained within an electromagnetic shielding encasement 252. The electromagnetic shielding encasement 252 comprises a coating of nanomagnetic particulate material (not shown) so designed as to respond to an electrostatic or time-varying magnetic field or effect, in a manner similar to that of liquid crystal display (LCD) materials. More specifically, these nanomagnetic particulate materials (not shown) are designed to shift alignment and to effect switching from a magnetic shielding orientation to a non-magnetic shielding orientation when a voltage is applied. Signal and power extraction element 210 preferably has means for providing a voltage to the shielding encasement 252 via line 254.

In another embodiment (not shown), the electromagnetic shielding encasement 252 of FIG. 7 may comprise a Faraday cage. In another embodiment (not shown), the electromagnetic shielding encasement 252 may comprise superparamagnetic material.

In another embodiment of this invention, catheter assembly 12 of FIG. 1 comprises additional means for allowing the positional tracking of the catheter assembly's 12 distal end 16 during a magnetic resonance procedure, e.g. during a magnetic resonance imaging procedure. In this case, the catheter may be so manufactured as to have narrow rings (not shown), e.g. having a length from about 0.5 millimeter to about 1 millimeter, equally spaced along the length of the catheter assembly 12. The rings (not shown) may be of a material, (e.g. gadolinium or other appropriate material) or combination of materials known to those skilled in the art which are visible in a magnetic resonance images without significantly distorting the applied magnetic fields in the immediate vicinity of the receiving coil(s) or antenna 30.

Figure 8A:
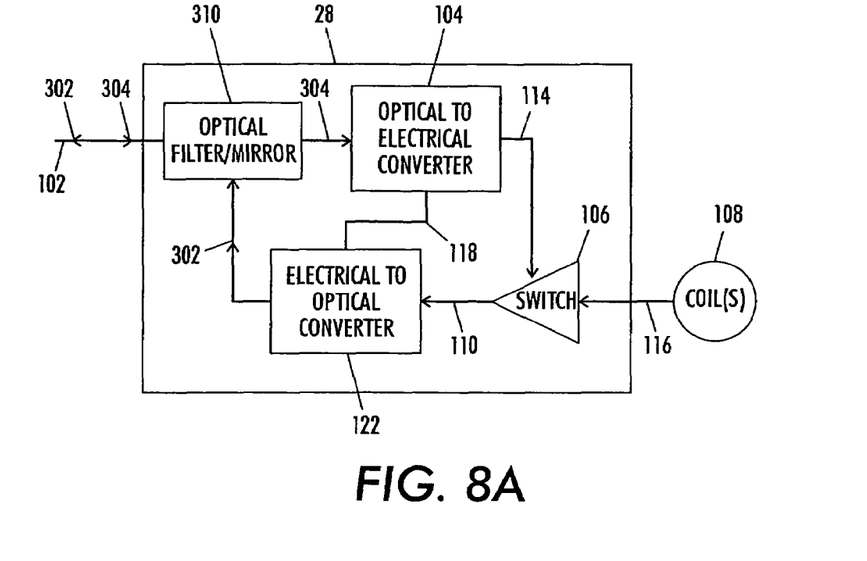
FIG. 8A is a block diagram of another design of the distal end of the catheter used in the device of FIG. 1.

In another preferred embodiment, as depicted in FIG. 8A, a single optic strand 102 is used for both transporting the optical command/gating signals 304 from the optical interface assembly 34 of FIG. 1 to the electronic assembly 28 as well as for transporting optical encoded signals 302 received from the coils 108 to the optical interface assembly 34 of FIG. 1. In this embodiment, and continuing to refer to FIG. 8A, an optical filter/mirror component 310 is added to the electronic assembly 28. The electrical to optical converter 122 receives an electrical signal 110 from the coil(s) 108 and converts it into an optical signal 302. Said optical signal 302 may be either a digital or an analog optical signal. Optical signal 302 is passed on to the optical filter/mirror component 310 which directs the optical signal 302 through the fiber optic strand 102. Optical signal 302 will have a fixed wavelength A1 while the optical command/gating signals 304 will have a different wavelength A2. The specific wavelengths to be used depends in part on the specific implementation of the optical filter/mirror 310.

Figure 8B:
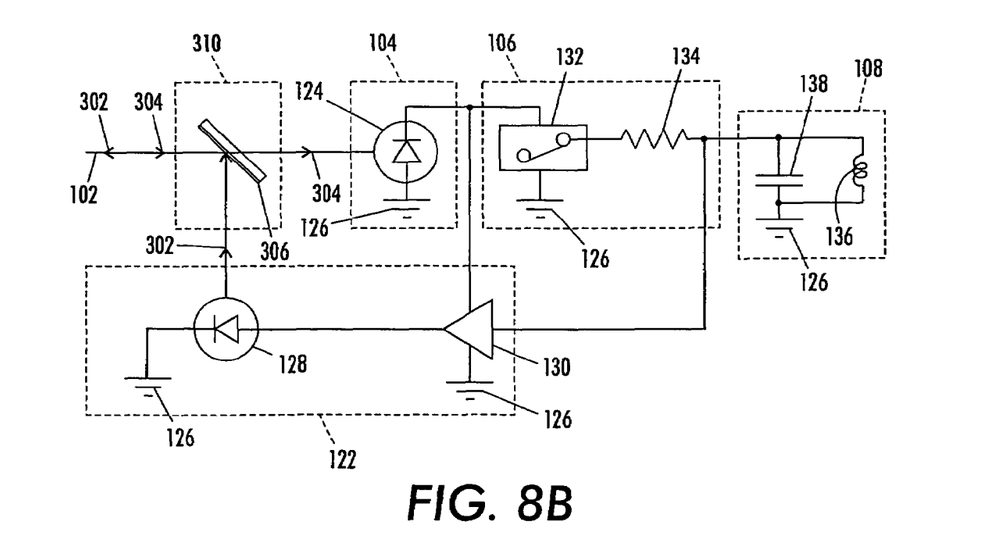
FIG. 8B is a schematic of the electronic components of the distal end.

FIG. 8B is a circuit diagram implementation for the embodiment depicted in FIG. 8A. Referring to FIG. 8B, and to the embodiment depicted therein, the optical filter/mirror 310 is implemented by element 306, which can be, e.g. a dichroic color filter, or a hot mirror, or a cold mirror. As is known to those skilled in the art, these optical elements are ready available for separating (reflecting and passing) and combining optical signals of different wavelengths. In one embodiment, optical filter/mirror 310 is a be a hot mirror 306 set at a 45 degrees angle to the incident optical signals 302 and 304 and which passes wavelengths, e.g., between about 450 nanometers to about 650 nanometers and reflects wavelengths, e.g., in the range of about 750 nanometers to about 1000 nanometers. Then wavelength A1 of optical signal 302 can be selected to be between 750 nanometers and 1000 nanometers so that optical signal 302 is reflected by hot mirror 306 while the wavelength A2 of optical signal 304 can be selected to be between 450 nanometers and 650 nanometers so that optical signal 304 is passed through hot mirror 306.

Figure 8C:
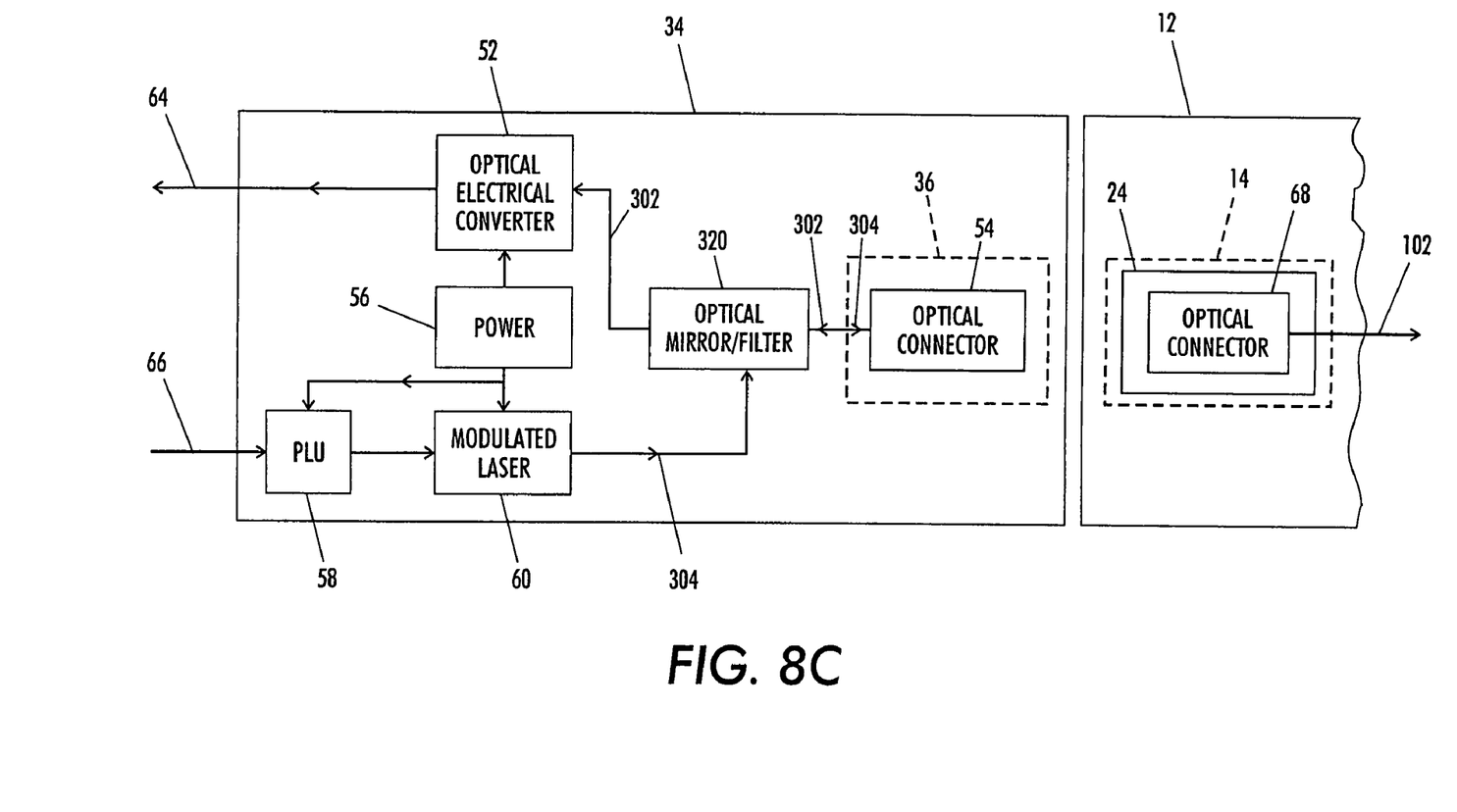
FIG. 8C is a block diagram of the Optical Interface wherein the catheter comprises a single optic strand.

FIG. 8C depicts the components for the optical interface assembly 34 for the case in which one optic strand 102 is used within the catheter assembly 12 for transporting both the magnetic resonance received signal 302 and the command/gating signal 304. In this embodiment, the optical interface assembly 34 comprises an optical mirror/filter which can be, e.g. a dichroic color filter, or a hot mirror, or a cold mirror.

The optical signal 302 is passed through the optical mirror/tilter to the optical to electrical converter 52, while the optical command gating/switching signal 304 from the modulated laser 60 is reflected by the optical mirror/tilter 320 into the optical connector 54. In one embodiment, optical tilter/mirror 320 is a cold mirror set at a 45 degree angle to the incident optical signals 302 and 304 and which reflects wavelengths, e.g., between about 450 nanometers to about 650 nanometers and passes wavelengths, e.g., in the range of about 750 nanometers to about 1000 nanometers. Then the wavelength A1 of optical signal 302 is preferably selected to be between about 450 nanometers and 650 nanometers so that optical signal 302 passes through cold mirror 320, while wavelength A2 of optical signal 304 is preferably selected to be between about 750 nanometers and 1000 nanometers so that optical signal 304 is reflected into optical connector 54 by cold mirror 306.

It is, therefore, apparent that there has been provided, in accordance with the present invention, an assembly for delivering optical signals comprising a nuclear magnetic resonance system; an optical interface assembly electrically connected to the nuclear magnetic resonance system, and a catheter assembly connected to the optical interface assembly. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. An assembly for delivering optical signals comprising a nuclear magnetic resonance system comprised of a magnet, an NMR programmable logic unit, a signal input channel, and a command output channel; an optical interface assembly electrically connected to said nuclear magnetic resonance system, said optical interface assembly comprising a first laser modulated so as to produce laser optical signals, an interface optical to electrical signal convertor; and a catheter assembly connected to said optical interface assembly, said catheter assembly comprising a proximal end, a distal end, a fiber optic cable assembly, an electronics assembly disposed at said distal end comprised of a catheter electrical to optical signal convertor and a catheter optical to electrical signal convertor, and a first receiving coil disposed at said distal end, wherein:

a. said NMR programmable logic unit of said nuclear magnetic resonance system sends command signals through said command output channel to said optical interface assembly for use in modulating said first laser;
   b. said laser optical signals received through said fiber optic cable assembly from said first laser are converted into catheter electrical signals by said catheter optical to electrical signal convertor;
   c. said first receiving coil is adapted to receive electromagnetic signals and deliver coil electrical signals to said electronics assembly of said catheter assembly;
   d. said coil electrical signals are converted by said catheter electrical to optical signal convertor to catheter optical signals and said catheter optical signals are delivered through said fiber optic cable assembly to said interface optical to electrical signal convertor; and
   e. said catheter optical signals are converted by said interface optical to electrical signal convertor into interface electrical signals and are delivered said signal input channel of said nuclear magnetic resonance system.

2. The assembly as recited in claim 1, wherein said optical interface assembly further comprises an interface programmable logic unit adapted to receive said command signals from said command output channel of said nuclear magnetic resonance system and to perform said modulating said first laser based upon said command signals.

3. The assembly as recited in claim 1, wherein said electronics assembly of said catheter assembly further comprises a switch for blocking or permitting the passage of said coil electrical signals to said catheter electrical to optical signal convertor.

4. The assembly as recited in claim 3, wherein said switch is opened by the delivery of light resulting from said modulating said first laser to said catheter optical to electrical signal convertor, said delivery of said light resulting from said modulating said first laser.

5. The assembly as recited in claim 4, wherein said assembly further comprises a second receiving coil, and wherein said switch is a multi-state switch used to select which of said first or second receiving coils provides said coil electrical signal to said electronics assembly of said catheter assembly based upon said modulating said first laser.

6. The assembly as recited in claim 1, wherein said catheter electrical to optical signal convertor further comprises a reference signal source.

7. The assembly as recited in claim 1, wherein said electronics assembly of said catheter assembly further comprises a detuning assembly adapted to change the resonance frequency of said first receiving coil.

8. The assembly as recited in claim 7, wherein said detuning assembly is operated in response to said command signals from said nuclear magnetic resonance system.

9. The assembly as recited in claim 7, wherein said electronics assembly of said catheter assembly further comprises a switch, and said detuning assembly further comprises at least one capacitor for which its capacitance changes with the application of a potential difference to said switch.

10. The assembly as recited in claim 9, wherein said switch is operated in response to said command signals from said nuclear magnetic resonance system.

11. The assembly as recited in claim 9, wherein said capacitance of said at least one capacitor is changed in response to said command signals from said nuclear magnetic resonance system.

12. The assembly as recited in claim 7, wherein said receiving coil further comprises a single inductive loop coil, and a tuning capacitor.

13. The assembly as recited in claim 12, wherein the capacitance of said tuning capacitor is changed in response to said command signals from said nuclear magnetic resonance system.

14. The assembly as recited in claim 7, wherein said electronics assembly of said catheter further comprises a command extraction component for filtering a detuning command to said detuning assembly.

15. The assembly as recited in claim 1, wherein said first receiving coil is selected from the group consisting of a pickup coil, a single loop coil, a multi-loop coil, a loopless antenna, and a dipole antenna.

16. The assembly as recited in claim 1, wherein said first laser provides electrical power to said electronics assembly of said catheter and control signals to said electronics assembly of said catheter.

17. The assembly as recited in claim 16, wherein said catheter optical to electrical signal convertor is comprised of a photovoltaic cell that converts light from said first laser into electrical power.

18. The assembly as recited in claim 1, wherein said optical interface assembly further comprises a second laser, and wherein said first laser generates optical command signals to said electronics assembly of said catheter and said second laser generates optical power for use by said electronics assembly of said catheter.

19. The assembly as recited in claim 18, wherein said catheter optical to electrical signal convertor is comprised of a photovoltaic cell that converts light from said second laser into electrical power.

20. The assembly as recited in claim 1, wherein said laser optical signals are comprised of digital optical signals.

21. The assembly as recited in claim 1, wherein said catheter optical signals are digital optical signals.

* * * * *